(12) United States Patent
Handa et al.

(10) Patent No.: US 9,327,024 B2
(45) Date of Patent: May 3, 2016

(54) POLYMER COATED FERRITE FINE PARTICLES AND METHOD FOR PREPARING POLYMER COATED FERRITE FINE PARTICLES

(75) Inventors: Hiroshi Handa, Tokyo (JP); Mamoru Hatakeyama, Kanagawa (JP); Satoshi Sakamoto, Kanagawa (JP); Hiroshi Kishi, Kanagawa (JP)

(73) Assignee: TOKYO INSTITUTE OF TECHNOLOGY, Tokyo (JP)

(*) Notice: Subject to any disclaimer, the term of this patent is extended or adjusted under 35 U.S.C. 154(b) by 1039 days.

(21) Appl. No.: 13/504,300

(22) PCT Filed: Oct. 28, 2010

(86) PCT No.: PCT/JP2010/006364
§ 371 (c)(1),
(2), (4) Date: Jun. 28, 2012

(87) PCT Pub. No.: WO2011/052205
PCT Pub. Date: May 5, 2011

(65) Prior Publication Data
US 2012/0269737 A1  Oct. 25, 2012

(30) Foreign Application Priority Data

Oct. 30, 2009 (JP) ................................ 2009-249902

(51) Int. Cl.
*A61K 41/00* (2006.01)
*A61K 9/50* (2006.01)
(Continued)

(52) U.S. Cl.
CPC ........... *A61K 41/0052* (2013.01); *A61K 9/5026* (2013.01); *A61K 9/5089* (2013.01);
(Continued)

(58) Field of Classification Search
None
See application file for complete search history.

(56) References Cited

U.S. PATENT DOCUMENTS

| 2010/0040553 A1* | 2/2010 | Abe ..................... A61K 9/5094 424/9.3 |
| 2011/0006245 A1 | 1/2011 | Handa et al. |

(Continued)

FOREIGN PATENT DOCUMENTS

| JP | 1-103631 | 4/1989 |
| JP | 2001-126909 | 5/2001 |

(Continued)

OTHER PUBLICATIONS

Wu et al., Magnetic Iron Oxide Nanoparticles: synthesis and surface functionalization strategies, Nanoscale Res Lett (2008) 3:397-415).*

*Primary Examiner* — Robert A Wax
*Assistant Examiner* — Melissa Mercier
(74) *Attorney, Agent, or Firm* — Greenblum & Bernstein, P.L.C.

(57) ABSTRACT

[Object] To provide a polymer coated ferrite fine particles being possible to control a particle size uniformly while having high aqueous dispersibility and preferred biomolecule immobilization ability and an easy method for preparing the same.

[Means Addressing Object] In an aqueous solvent, iron ion is protected by chelating polyacrylic acid and then alkaline is added. Thereafter, a reaction system is heated under pressurized condition to produce simultaneous precipitation of the ferrite fine particles and coating thereof. As the result, the polymer coated ferrite fine particles having uniform particle size may be prepared in one step with excellent reproducibility. The polymer coated ferrite fine particles of the present invention has high water dispersibility and has preferred biomolecule immobilization performance by carboxyl groups coming from the polyacrylic acid.

20 Claims, 11 Drawing Sheets

(51) Int. Cl.
  *A61K 47/02* (2006.01)
  *A61K 49/18* (2006.01)
  *B82Y 5/00* (2011.01)
  *B82Y 25/00* (2011.01)
  *C01G 49/00* (2006.01)
  *C01G 49/08* (2006.01)
  *C09C 1/22* (2006.01)
  *C09C 1/24* (2006.01)
  *B82Y 30/00* (2011.01)
  *H01F 1/00* (2006.01)
  *H01F 1/34* (2006.01)

(52) U.S. Cl.
  CPC ............... *A61K 9/5094* (2013.01); *A61K 47/02* (2013.01); *A61K 49/1854* (2013.01); *B82Y 5/00* (2013.01); *B82Y 25/00* (2013.01); *B82Y 30/00* (2013.01); *C01G 49/0072* (2013.01); *C01G 49/08* (2013.01); *C09C 1/22* (2013.01); *C09C 1/24* (2013.01); *H01F 1/0054* (2013.01); *C01P 2004/03* (2013.01); *C01P 2004/64* (2013.01); *H01F 1/344* (2013.01)

(56) References Cited

U.S. PATENT DOCUMENTS

| 2011/0183355 | A1 | 7/2011 | Handa et al. |
| 2011/0183555 | A1 | 7/2011 | McCammon |

FOREIGN PATENT DOCUMENTS

| JP | 2005-60221 | 3/2005 |
| JP | 2006-88131 | 4/2006 |
| JP | 2007-216134 | 8/2007 |
| JP | 2007-308548 | 11/2007 |
| JP | 2008-127454 | 6/2008 |
| JP | 2008-280277 | 11/2008 |
| JP | 2009-114066 | 5/2009 |
| WO | 2008/081917 | 7/2008 |

* cited by examiner

POLYMER COATED FERRITE FINE PARTICLES AND METHOD FOR PREPARING POLYMER COATED FERRITE FINE PARTICLES

TECHNICAL FIELD

The present invention relates to a functional magnetic fine particle and more particularly relates to a multifunctional polymer coated ferrite fine particles and a method for preparing the polymer coated ferrite fine particles.

BACKGROUND ART

Recently, various developments have been made about structures of surface carted magnetic fine particles which are intended to be used for an MRI imaging agent or a thermal source of hyperthermia therapy. JP 2009-114066 (patent literature 1) discloses the method comprising the steps of adding an iron ion solution (ferrous and ferric irons) to an aqueous solution of dextran as a coating material, adding an aqueous solution of sodium hydroxide and then heating and refluxing to prepare dextran magnetite.

FIG. 11 shows a schematic reaction mechanism in the preparation method of the patent literature 1. In the conventional method described in the patent literature 1, the iron ions in the reaction system precipitate to form the magnetite fine particles 50 by adding sodium hydroxide (alkaline) and these immediately coagulate as shown in FIG. 11. In the conventional methods, the dextran molecule 52 coats the coagulants and particle sizes of final products become as large as several tens nm such that there were limitations on improvements in making fine size particles and also in improving dispersibility. In addition, according to the conventional method, the coagulation occurred unevenly and hence it was difficult to control particle sizes evenly.

On the other hand, though the introduction of various biomolecules on the surface on the surface coated magnetic fine particles for biological applications, additional surface modification processing must be required in order to introduce functional groups on the surface of the magnetic fine particles in the case of the conventional surface coated magnetic fine particles.

PRIOR ART LITERATURE

Patent Literature

Patent Literature 1: JP 2009-114066

SUMMARY OF INVENTION

Object Addressed by Invention

The present invention has been completed by considering the problems in the above conventional art and an object of the present invention is to provide polymer coated ferrite fine particles having high aqueous dispersibility and a preferable biomolecule immobilizing performance as well as having a performance for uniform particle size control.

Means for Addressing Object

The inventors have been studied about the polymer coated ferrite fine particles having high aqueous dispersibility and a preferable surface modification ability as well as having the performance for uniform particle size control and have completed the present invention with finding that uniform particle sized polymer coated ferrite fine particles may be prepared in large amounts with excellent reproducibility in one stage by using the steps of adopting polyacrylic acid including rich carboxylic acid groups as the coating polymer component of the ferrite fine particles; adding alkaline after protecting the polyacrylic acid by chelating the polyacrylic acid to ferrous iron ions in aqueous solvent; and then heating under pressurized condition.

According to the present invention, a method for preparing polymer coated ferrite fine particles may be provided. The method comprises the steps of: preparing a mixed aqueous solution dissolving therein ferrous iron ion and polyacrylic acid; adding alkaline to the mixed aqueous solution; adding an oxidizer to the mixed aqueous solution after addition of the alkaline; and heating the mixed aqueous solution after addition of the oxidizer under pressure. The oxidizer may be sodium nitrate and pH of a reaction system may be adjusted to be from 10.5 to 11.0. The mixed aqueous solution may be preferably heated in a temperature condition beyond 100 Celsius degrees and more particularly, the mixed aqueous solution may be heated under the pressure in a pressure proofed close packing container and the temperature condition may lie between 150 Celsius degrees and 200 Celsius degrees. According to the present invention, the mixed aqueous solution may be prepared to form the chelate between the carboxylic acid of the polyacrylic acid and the ferrous iron and the mixed aqueous solution may be prepared in an equivalent ratio of a carboxyl group of the polyacrylic acid to the ferrous iron ion to be from 1.2 to 1.8. A molecular weight of the polyacrylic acid may preferably range from 1000 to 4000. Furthermore, the present invention may use a mixed aqueous solution comprises the step of preparing the mixed aqueous solution dissolving at least one kind of metal ion selected from the group consisting of zinc, nickel, cobalt, manganese, barium, rare earth metal other than the ferrous iron ion as a starting solution.

Further according to the present invention, a polymer coated ferrite fine particle and the aqueous dispersion thereof may be provided. The ferrite fine particles may be coated with polyacrylic acid and have an average particle size not more than 10 nm; the polymer coated ferrite fine particles may have a T1 relaxation performance from 60 to 70 $(mMsec)^{-1}$ and a T2 relaxation performance from 110 and 130 $(mMsec)^{-1}$. The polymer coated ferrite fine particles of the present invention may be used as an MRI imaging agent or as a heat source for hyperthermia therapy. In addition, the polymer coated ferrite fine particles of the present invention may exhibit a magneto-acoustic effect.

Technical Advantage

As described above, according to the present invention, a polymer coated ferrite fine particle having high aqueous dispersibility and a preferable biomolecule immobilizing performance as well as having the ability for uniform particle size control and the method for preparing the same may be provided.

EMBODIMENT FOR PRACTICING INVENTION

Figure 1:
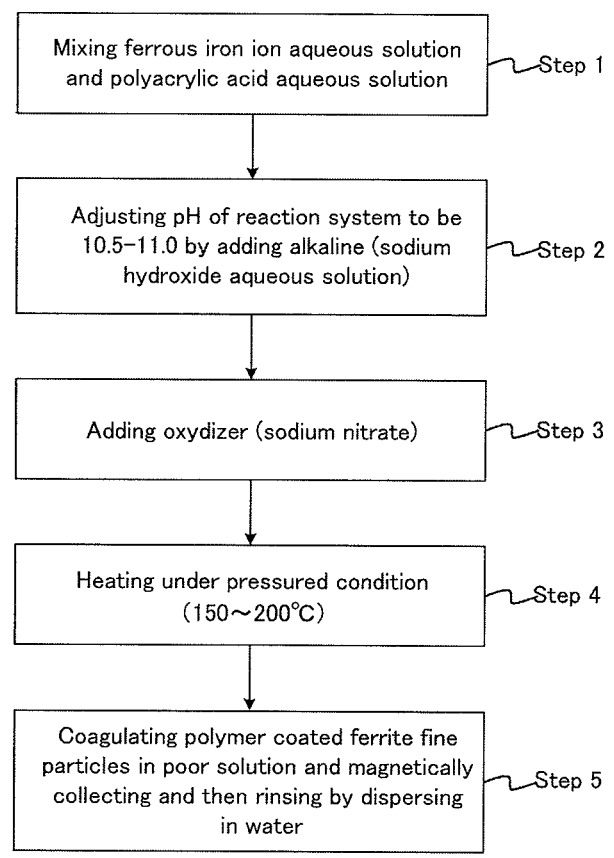
FIG. 1 shows the flowchart of the present preparation method.
Figure 2:
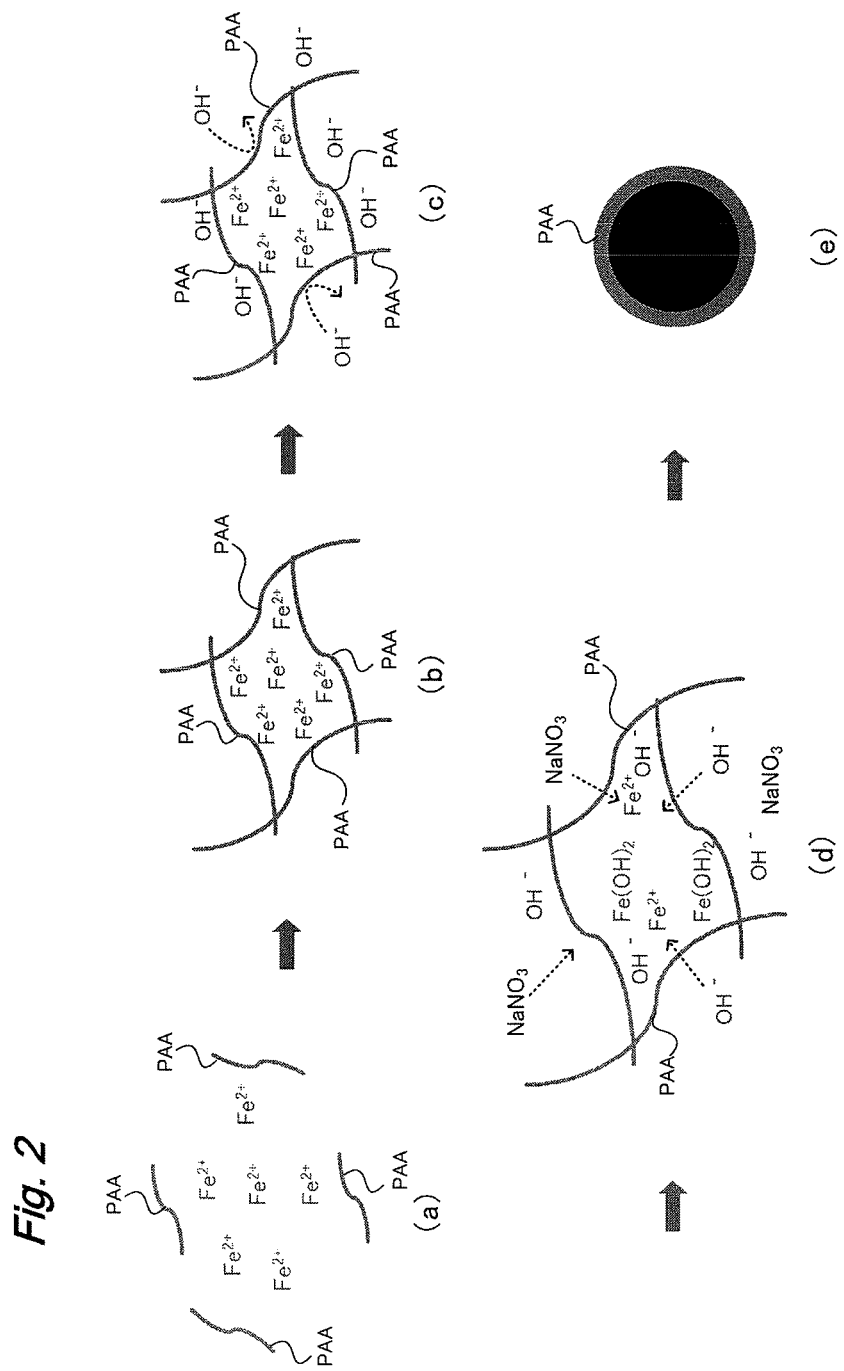
FIG. 2 shows a schematic mechanism of the reaction mechanism.

Now hereunder, the preparation method of the present polymer coated ferrite fine particles will be explained with referring to FIGS. 1 and 2. Here, FIG. 1 shows the flowchart of the present preparation method and FIG. 2 shows a schematic mechanism of the reaction mechanism.

(Process 1)

First, the aqueous admixture dissolved therein ferrous iron ions and polyacrylic acid is prepared. More particularly, the aqueous solutions of ferrous irons and polyacrylic acid may be mixed and stirred to prepare the aqueous admixture. The ferrous iron aqueous solution may be prepared by foe example, dissolving iron (II) chloride tetra hydrate in ultra pure water from which the dissolved oxygen is purged. The aqueous solution of the polyacrylic acid may similarly be prepared by foe example, dissolving iron (II) chloride tetra hydrate in ultra pure water from which the dissolved oxygen is purged.

When the ferrous iron solution and the aqueous solution of polyacrylic acid are sufficiently mixed and stirred, the reaction system transits from the condition shown in FIG. 2(a) to (b). That is to say, the polyacrylic acid (PAA) dissolved in the reaction system forms the complex by chelating the carboxylic acids to the ferrous iron ion ($Fe^{2+}$) similarly dissolved in the reaction system. The structure of the polyacrylic acid is described below.

[Chemical 1]

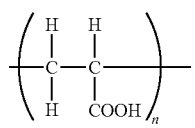

As described in the above chemical formula, polyacrylic acid includes many carboxylic acid groups and the carboxylic acid ionized in the aqueous solution to form carboxylate anion and hence, the polyacrylic acid shows high chelate formation ability to the iron ion. Therefore, the polyacrylic acid promptly surrounds the ferrous irons when mixed therewith to form the chelate complex. In the present invention, the chelate complex becomes a precursor of the polymer coated ferrite fine particles. According to the present invention, it may be preferred to prepare the mixed aqueous solution such that the carboxylic acid groups in the polyacrylic acid may stoichiometrically present in slightly excess amounts to the amounts of the ferrous iron ion so as to form preferably the above chelate complex. More particularly, it may be preferred to prepare the mixed aqueous solution in the equivalent ratio of the carboxylic acids in the polyacrylic acid to the ferrous iron ions to be from 1.2 to 1.8.

Here, the polyacrylic acid of the present invention may refer any compound which ionize to form the carboxylate anion in water and may include salts such as sodium polyacrylate as well as the polyacrylic acid. In addition, the molecular weight of the polyacrylic acid may be adequately selected depending on targeted particle sizes. That is to say, the total diameter if the final product may become large depending on the molecular weight of the selected polyacrylic acid and for example, when one may expect to control the total diameter of the final product to be not more than 10 nm, the molecular weight of the polyacrylic acid may range between 1000 and 4000.

(Process 2)

Next, the alkaline such as aqueous sodium hydroxide solution is added. This alkaline is added as the conventional trigger for precipitating ferrite similar to the conventional coprecipitation. In the present method, the polyacrylic acid tightly surrounds and chelates the ferrous iron ions after the process 1, and hence the reaction with the added alkaline ($OH^-$) and iron ion ($Fe^{2+}$) may be inhibited by the polyacrylic acid (PAA) as shown in FIG. 2(c). Therefore, the present invention may provide uniform alkaline concentration of the reaction system while maintaining the condition of inhibiting the reaction between iron ion ($Fe^{2+}$) and the alkaline. According to the present invention, it may be preferred to optimize the pH of the reaction system when the alkaline is added. The details will be described later.

(Process 3)

In order to form ferrite, ferrous iron ion ($Fe^{2+}$) and ferric iron ion ($Fe^{3+}$) are necessary. In the present invention, first only the ferrous iron is present, and hence the oxidization of a part of the ferrous iron ion must be necessary to prepare the ferric iron ion ($Fe^{3+}$). Then in the process 3, an oxidizer is added to the reaction system. According to the present invention, the oxidizer may include sodium nitrate ($NaNO_3$), oxygen, hydrogen peroxide etc. Particularly, sodium nitrate ($NaNO_3$) is more preferred as the oxidizer of the present invention because $NaNO_3$ has relatively low oxidizing power and its dose may be easily controlled due to its powdery condition such that the oxidization degree may be easily controlled. By the addition of oxidizer, the ferrous iron ion in the region surrounded by the polyacrylic acid is gradually oxidized and a part thereof is oxidized to ferric iron ions ($Fe^{3+}$).

(Process 4)

However, the condition in which the polyacrylic acid is chelated to the iron ions, the phase transition to magnetite is inhibited and the reaction may hardly occur. Therefore, the reaction must be accelerated by an external stimulation. Then, the reaction system may be heated in the present invention. As the result, the reaction occurs along with the following mechanism: That is to say, the thermal motion of $OH^-$ ion becomes intense by heating the reaction system and the $OH^-$ ion penetrates to the region surrounded by the polyacrylic acid (PAA) and reacts with the ferrous iron ($Fe^{2+}$) to form $Fe(OH)_2$. $Fe(OH)_2$ thereafter provides $Fe_3O_4$ by the phase transition. On the other hand, the ferric iron ion ($Fe^{3+}$) is present in the above region by the aforementioned oxidizer and $Fe_3O_4$ may be formed by the reaction among $Fe^{3+}$ in the region the ferrous iron ion ($Fe^{2+}$) and the $OH^-$ ion. As the result, the ferrite fine particles with excellent quality in the region surrounded by the polyacrylic acid (PAA) may be formed. This point will be detailed hereunder.

When the ferrite fine particles are formed by the conventional coprecipitation method, alkaline ($OH^-$) is added to the initial solution including the mixture of the ferrous iron ion ($Fe^{2+}$) and the ferric iron ion ($Fe^{3+}$); however, this method can not avoid the reaction between sole ferric iron ion ($Fe^{3+}$) and alkaline ($OH^-$) and then $Fe(OH)_3$ which does not contribute the formation of the ferrite may be present in a few amounts. The $Fe(OH)_3$ mixed into the fine particles may be the origin for degradation of crystal quality and magnetization.

In this regard, in the present preparation method, the initial solution does not contain the ferric iron ion ($Fe^{3+}$) and hence, $Fe(OH)_3$ could not almost be formed. Then, the present method may be possible to precipitate the ferrite fine particles with excellent crystal quality and with high magnetization.

As more preferable aspect of the present invention, the polyacrylic acid (PAA) is adsorbed to the ferrite fine particles almost immediately after the formation of the ferrite fine particles. Then, the precipitated ferrite fine particles has no chance for coagulating among the ferrite fine particles each other such that the coating per single particle of the precipitated ferrite fine particles may be realized. If coating molecules with less adsorption ability is used, the $OH^-$ ion adsorbs on the ferrite particle surface with higher priority than the coating molecules and then, coating substances could not remained on the ferrite fine particles after the reaction. Contradictory to the above conventional scheme, the present invention adopts the polyacrylic acid which exhibits high adsorption ability to the ferrite fine particle surface as the coating molecule. The polyacrylic acid (PAA) is adsorbed to the ferrite fine particles almost immediately after the formation of the ferrite fine particles.

Here, according to the present invention, higher temperature of this heating process may provide ferrite fine particles with more excellent crystal quality. In the present invention, the mixed aqueous solution may be preferably heated at the temperature condition above 100 Celsius degrees. Particularly, the mixed aqueous solution may be preferable heated under the pressurized condition in a pressure proofed closed container and the temperature condition of the heating may be set between 150 Celsius degrees and 200 Celsius degrees.

Furthermore, it may be preferred to optimize pH of the reaction system when the alkaline is added in the present invention. If the alkaline ($OH^-$ ion) is too poor in the reaction system, sufficient precipitation of the ferrite may become insufficient and in turn, when the alkaline is too excess in the reaction system, the $OH^-$ ion is adsorbed to the surface of the ferrite particle with higher priority than that of the coating molecule such that the coating molecule may not remain on the surface of the ferrite fine particle. Since the present invention optimizes the pH in the preceding process 2, the above unexpected cases may be avoided. By adjusting the pH of the reaction system between 10.5 and 11.0 according to the present invention, the ferrite with excellent crystal quality may be obtained and the ferrite fine particles may be coated in the primary particle state as shown in FIG. 2(e).

(Process 5)

Lastly, a poor solvent such as 1,4-dioxane or alcohols is added to the reaction solution to coagulate the formed polymer coated ferrite fine particles and then the ferrite fine particles are magnetically collected. The particles are again dispersed and rinsed in the ultra pure water to obtain a water dispersion of the present polymer coated ferrite fine particles.

According to the present invention, since the ferrite fine particles are precipitated from the reaction solvent which is mixed evenly, the crystal formation and growth may synchronously occur for all of the particles. Then, the homogeneity may be reflected to the sizes of the polymer coated ferrite fine particles as the final products. In addition, the precipitation of the ferrite fine particles and the coating thereof may occur synchronously such that the precipitated ferrite fine particles do not form secondary particles and the particle size of the final products (total diameter) may be controlled less than 10 nm.

The present polymer coated ferrite fine particles obtained by the above procedures has significantly finer particle sizes than the conventional ones while exhibiting excellent aqueous dispersibility. In addition, the coating layer comprising the polyacrylic acid has many carboxylic acid groups on the surface and exhibits high immobilization ability as is to biomolecules such that additional surface modifications may not required.

Furthermore, the present polymer coated ferrite fine particles have high magnetization and exhibit high imaging ability in which T1 relaxation performance is to be 60-70 ($mMsec^{-1}$) and T2 relaxation performance is to be 110-130 ($mMsec^{-1}$); these may be the most suitable for a MRI imaging agent. At the same time, the present polymer coated ferrite fine particles has a high heat generation property which may be the most suitable for a heat source of the hyperthermia therapy.

Moreover, the present preparation method may provide an advantage in production costs because the present method may form large amounts of polymer coated ferrite fine particles in one step and in excellent reproducibility by starting from fewer starting materials than those of the conventional method.

As said hereinbefore, the present polymer coated ferrite fine particles have been explained and according to the present invention, polymer coated ferrite fine particles including metal atoms other than iron may be prepared. More particularly, using the mixed solution in the process 1 comprising zinc, nickel, cobalt, manganese, barium or rare-earth metal ions such as samarium as well as ferrous iron ion as the starting solution, the ferrite fine particles including metal atoms other than iron with arbitrary ratios may be precipitated and the particles may be coated by the polyacrylic acid for synthesizing the polymer coated ferrite fine particles.

EXAMPLES

Now, the present polymer coated ferrite fine particles will be more concretely explained using practical examples; however, the present invention must not be limited to the following examples.

(Preparation of Polymer Coated Ferrite Fine Particle)

The polymer coated ferrite fine particles of the present invention were prepared by the following procedures: Here, each of the processes described below were conducted under an ambient temperature as far as otherwise noted. First, 0.8 g of polyacrylic acid with molecular weight 2000 was added to 60 ml of ultra pure water followed by bubbled for 30 min. with nitrogen gas in order to purge oxygen. Separately, iron (II) chloride tetra hydrate 0.67 g was added and dissolved to 40 ml of ultra pure water 40 bubbled with the nitrogen gas and then, the prepared solution was added and mixed with stirring to the above prepared polyacrylic acid solution (equivalent ratio of polyacrylic acid to iron (II) chloride tetra hydrate was to be 1.5).

The above mixed solution was stirred for 5 min. and then to this mixed solution 0.33N sodium hydroxide 40 ml bubbled with nitrogen gas for 30 min beforehand was added and further then pH of the reaction system was adjusted in the range between 10.5 and 11.0.

Sodium nitrate 0.1 g was added to the pH adjusted mixed solution and the mixture was stirred for 5 min. Then the mixed solution was transferred to a pressure proofed container and kept for 8 hours in an oven from 150 Celsius degrees to 200 Celsius degrees. Finally, 1,4-dioxane (poor solvent) was added to the reaction solution to coagulate the magnetic fine particles and the magnetic fine particles were then collected magnetically. After that, the particles were again dispersed in ultra pure water and rinsed to prepare aqueous dispersion of the example polymer coated ferrite fine particles.

Here, as a comparative example, polymer coated ferrite fine particles were prepared by using the method in which the polyacrylic acid was provided after the preparation of ferrite particles. First, ferrite nano particles were prepared by the coprecipitation method. An average particle size thereof was about 7 nm from the results of analysis of electron microscope images. 60 mg of the ferrite nano particles was sonicated for about one our in 0.8M polyacrylic acid solution of pH 7 and then the ferrite nano particles were rinsed by ultra pure water to prepare aqueous dispersion of the polymer coated ferrite fine particles.

Figure 3:
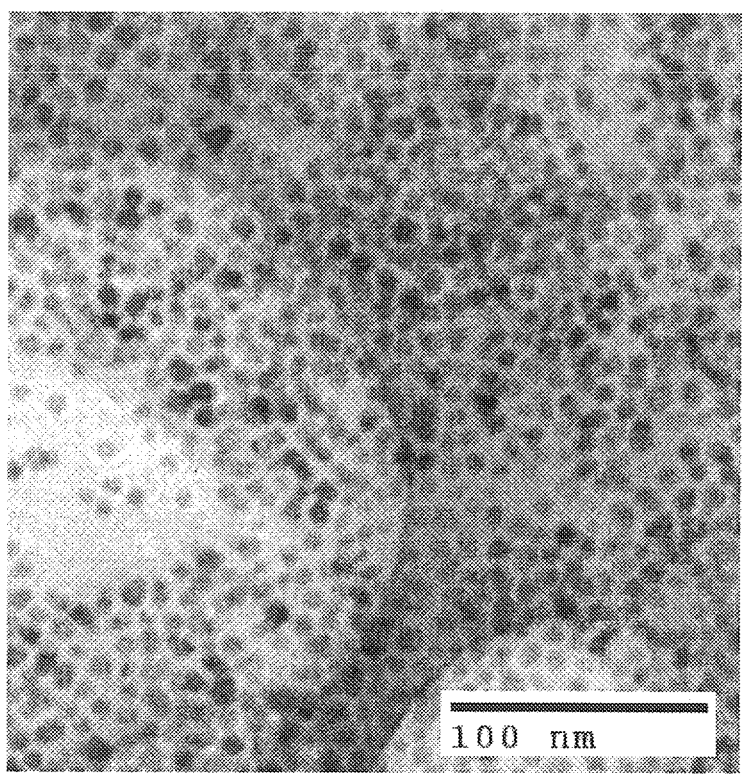
FIG. 3 shows the electron microscope images of the polymer coated ferrite fine particles of the example.
Figure 4:
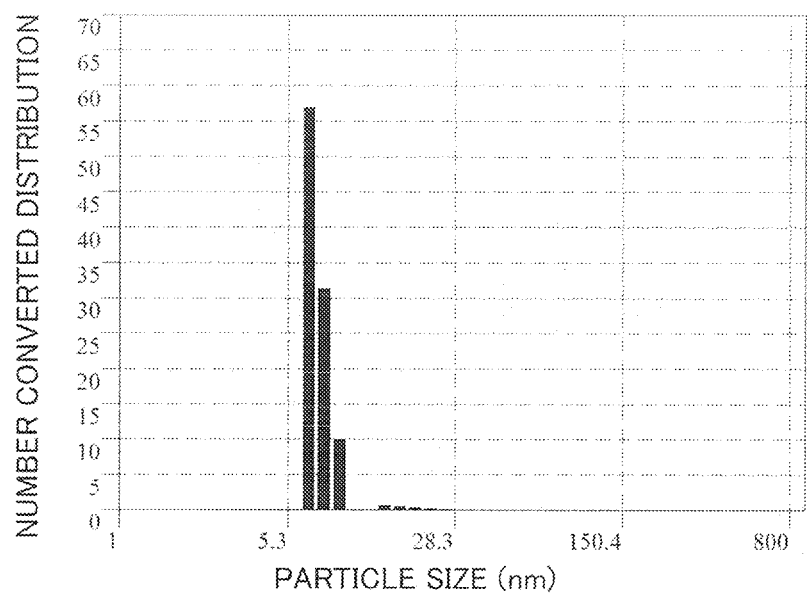
FIG. 4 shows the number converted average particle size distribution of the polymer coated ferrite fine particles of the example.

FIG. 3 shows the electron microscope images of the polymer coated ferrite fine particles of the example. As the results of observation by the electron microscope, the polymer coated ferrite fine particles revealed to have a uniform particle size and presented in the monodispersity. Furthermore, results of analysis by a dynamic light scattering method, the average particle size (number converted) of the example polymer coated ferrite fine particles in the dispersion media was to be 6.9±1.6 nm. FIG. 4 shows the number converted average particle size distribution of the polymer coated ferrite fine particles of the example.

Figure 5:
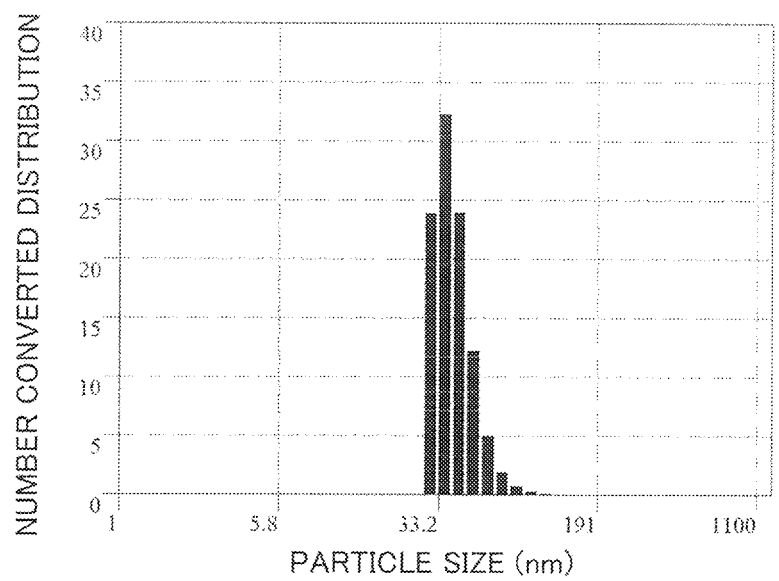
FIG. 5 shows he number converted average particle size distribution of the polymer coated ferrite fine particles of the comparative example.

On the other hand, the results of analysis by the dynamic light scattering method of the comparative example, the average particle size (number converted) of the comparative example polymer coated ferrite fine particles in the dispersion media was to be 36.9±8.9 nm and this value was significantly larger than that of example. This was supposed that the polyacrylic acid was adsorbed on particle coagulates of the single ferrite particle. FIG. 5 shows he number converted average particle size distribution of the polymer coated ferrite fine particles of the comparative example.

Figure 6:
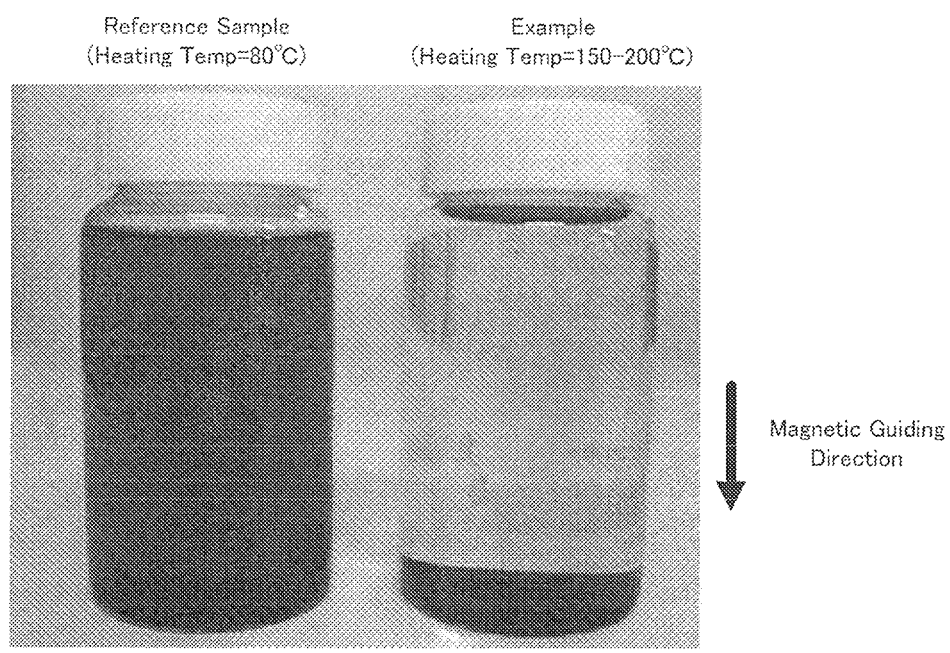
FIG. 6 shows photographs of magnetic collection prepared by the reference heating condition (80 Celsius degrees).
Figure 7:
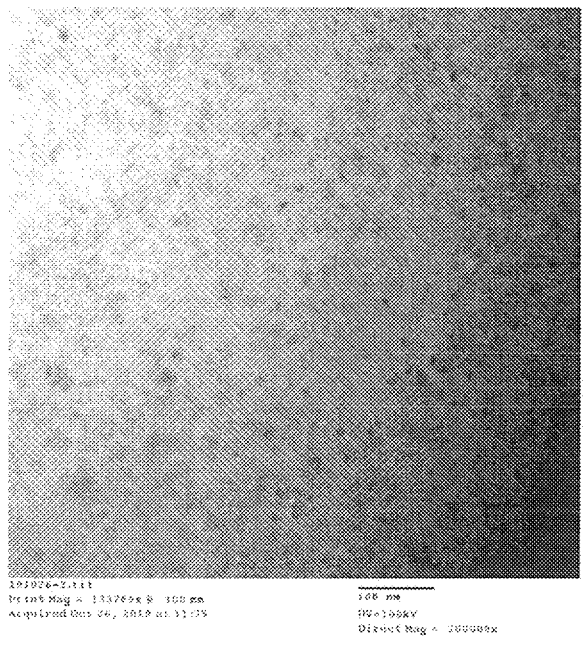
FIG. 7 shows the electron microscope image of the dispersion prepared at the reference heating condition.

Here, as a reference sample, the dispersion prepared by placing the mixed solution prepared by the similar process with the above example in an autoclave kept at 80 Celsius degrees for 8 hours was examined. FIG. 6 shows photographs of magnetic guiding to the perpendicularly lower direction for each of the dispersions; one is prepared by the reference heating condition (80 Celsius degrees) and the other is prepared by the heating condition of the example (150-200 Celsius degrees). As shown in FIG. 6 (right hand photograph), all of the particles contained in the dispersion prepared by the heating condition of the example (150-200 Celsius degrees) are drawn to the bottom of the sample tube and the top clear layer is completely transparent. On the other hand, the dispersion prepared by the reference heating condition (80 Celsius degrees) shows the turbid and brown upper layer in spite of the magnetic guiding as shown in FIG. 6 (left hand photograph). Furthermore, FIG. 7 shows the electron microscope image of the dispersion prepared at the reference heating condition (80 Celsius degrees). As the result of observation by the electron microscope, needle crystals, which may be iron hydroxide (non-magnetized phase), were observed. From the above results, the non-magnetized phase other than magnetite may be synthesized in large amounts when the reaction is conducted under the heating condition of the reference example (80 Celsius degrees).

(Evaluation of Imaging Ability)

With respect to the present polymer coated ferrite fine particles, the imaging performance was evaluated by MRI (1.5 T). As the results, the T1 relaxation performance was 64.1 (mMsec$^{-1}$) and the T2 relaxation performance was 122.6 mMsec$^{-1}$). The saturation magnetization was measured to be 70 emu/g.

(Evaluation of Hyperthermia Therapy Performance)

Figure 8:
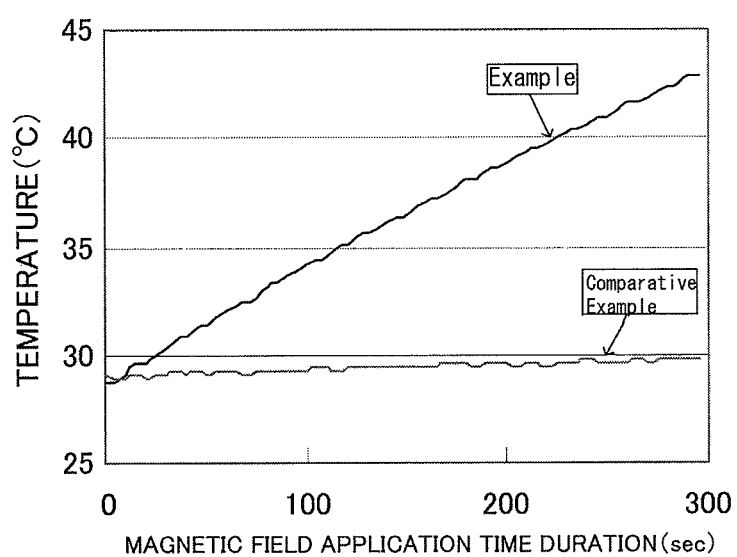
FIG. 8 shows the relations between the temperatures of both samples (Celsius degrees) and the magnetic field application time duration (sec).

The aqueous dispersion of the present polymer coated ferrite fine particle and the aqueous dispersion of the comparative example were each separated into plastic bottles and then pure water was added to prepare samples (iron concentration=40 mM). The plastic bottles containing respective samples were placed in a coil and then applied with the magnetic field and then temperatures of the samples were measured by an optical fiber thermometer. The frequency of the alternative magnetic field applied was 900 kHz and the magnetic field strength was fixed to be 55 Oe. FIG. 8 shows the relations between the temperatures of both samples (Celsius degrees) and the magnetic field application time duration (sec). As shown in FIG. 8, the temperature of the example sample rises to 42.5 Celsius degrees which is the target temperature of the hyperthermia therapy in the short time duration as short as 300 sec while the temperature of the comparative example sample hardly rose.

(Evaluation of Biomolecule Immobilization Performance)

Figure 9:
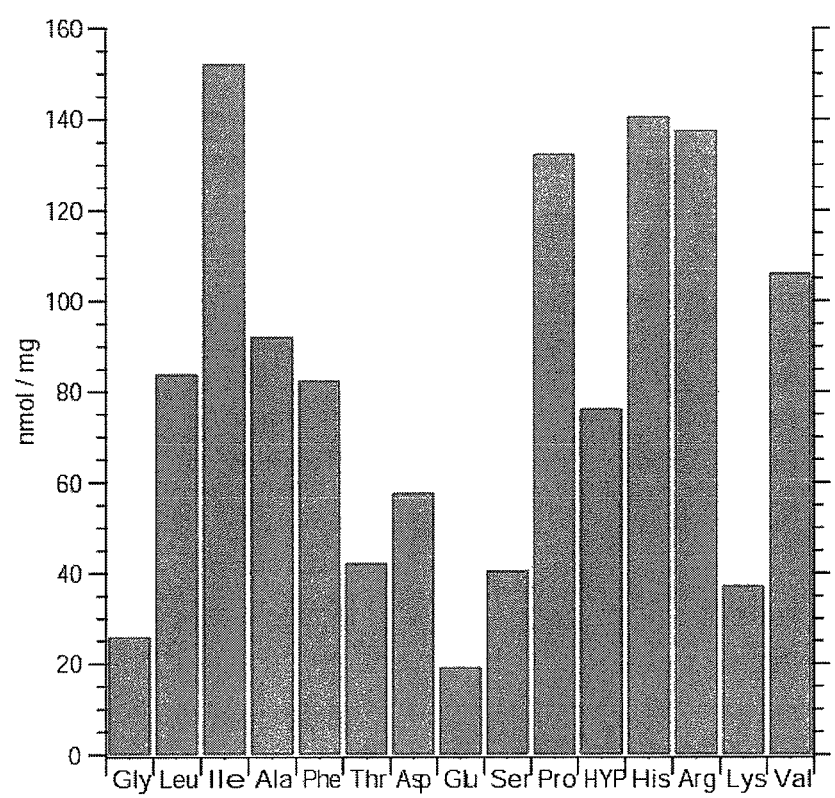
FIG. 9 shows the amino acid immobilized amounts (mmol) per 1 mg of the present polymer coated ferrite fine particles for each of the amino acids.

To 1 mg of the present polymer coated ferrite fine particles, various kinds of amino acids 100 mmol of which carboxylic groups were protected, 1-(ethyl)-3-(3-dimethylaminopropyl) carbodiimide hydrogen chloride 10 mmol, and 1-hydroxybenzotriasol 10 mmol respectively and the mixture were reacted for 2 hours in water and at the ambient temperature. After the reaction, the immobilization of amino acids on the polymer coated ferrite particle surface. FIG. 9 shows the amino acid immobilized amounts (mmol) per 1 mg of the present polymer coated ferrite fine particles for each of the amino acids. As shown in FIG. 9, it was found that the biomolecule might be easily immobilized on the surface of the present polymer coated ferrite fine particles.

(Examination of Magneto-Acoustic Effect)

Figure 10:
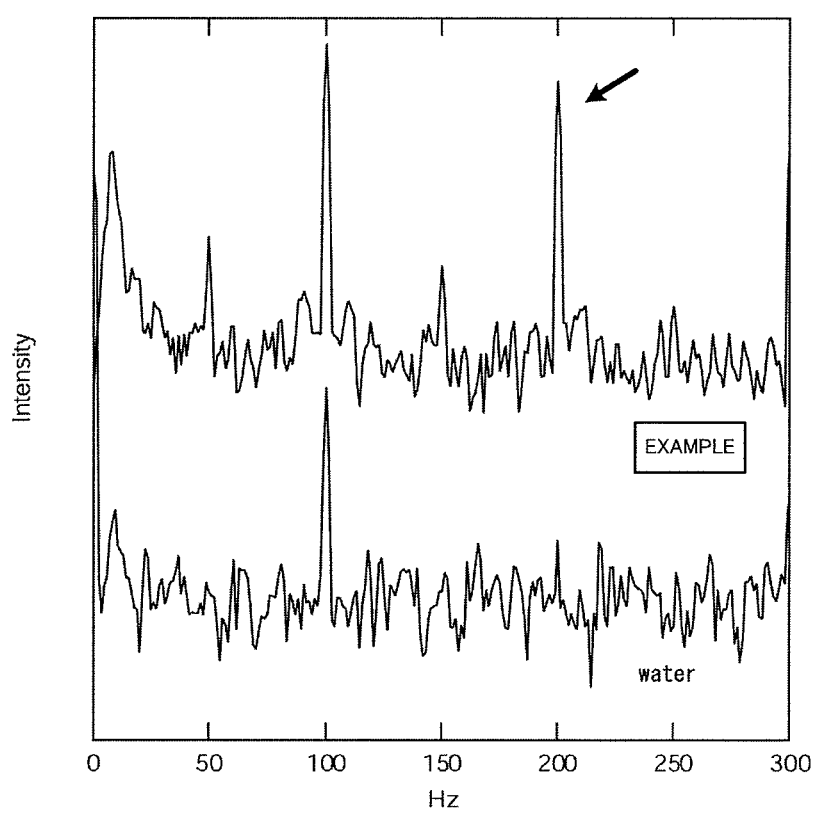
FIG. 10 shows the sound strength generated by the present polymer coated ferrite fine particles when the alternative magnetic field of the frequency of 100 Hz was applied.
Figure 11:
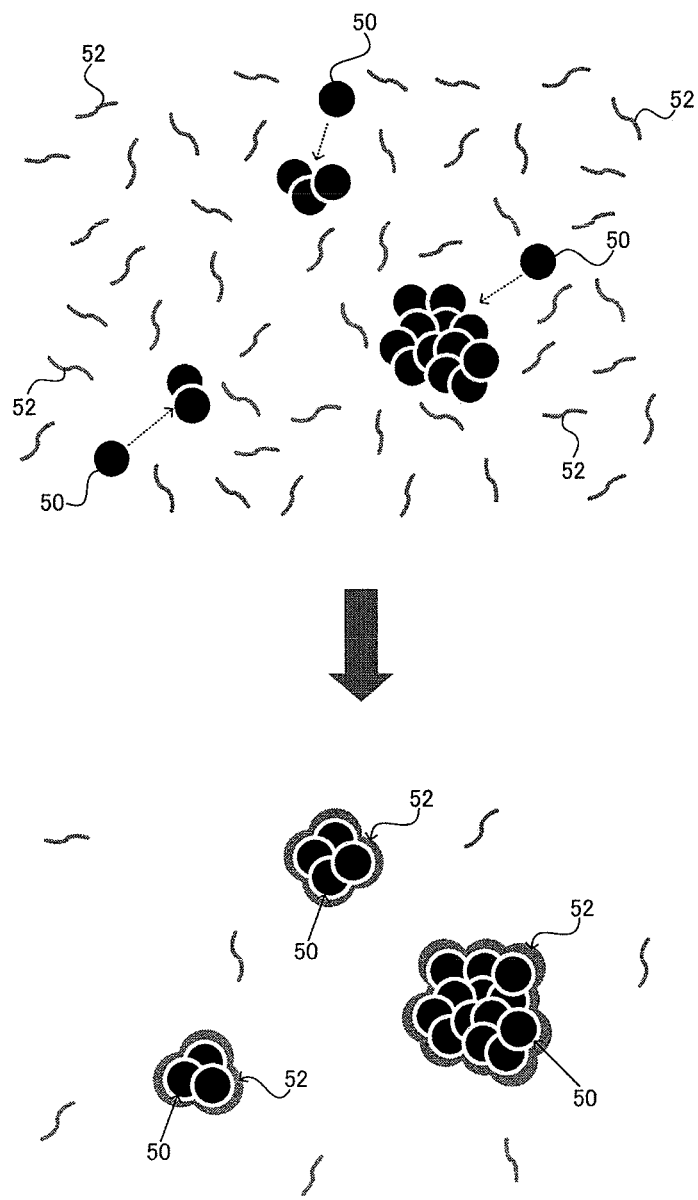
FIG. 11 shows a schematic reaction mechanism in the preparation method of the patent literature 1.

The phenomenon was known that the ferrite particles placed in the alternative magnetic field generated the sound having the doubled frequency of the input frequency and the inventors was examined the magneto-acoustic effect about the present polymer coated ferrite fine particle. FIG. 10 shows the sound strength generated by the present polymer coated ferrite fine particles when the alternative magnetic field of the frequency of 100 Hz was applied. In FIG. 10, the result which was observed by applying the same alternative magnetic field to water as the contrast example is shown. As indicated by the arrow in FIG. 10, the sound having 200 Hz was generated from the present polymer coated ferrite fine particles such that the present polymer coated ferrite fine particles may work as a sound marker as well as the magnetic marker function.

(Preparation of Polymer Coated Ferrite Fine Particles Doped with Other Metal)

Using the similar procedure described above, 0.1 M ferrous iron ion solution was prepared by adding and dissolving 0.6 g of iron (II) chloride tetra hydrate to the ultra pure water 30 ml to prepare 0.1 M ferrous iron ion solution. On the other hand, 0.136 g of zinc chloride was dissolved in the oxygen purged ultra pure water 10 ml to prepare 0.1 M zinc solution. Then the zinc solution (0.7 ml) and the above ferrous iron ion solution (7.7 ml) were mixed to prepare the metal ion solution. To this metal ion solution, the above described polyacrylic acid solution was added and mixed under stirring to provide the starting solution. The following processes were conducted as described above. As the result, the polymer coated ferrite fine particles containing the ferrite which 8% out of the total iron was replaced by zinc were obtained.

INDUSTRIAL APPLICABILITY

As described above, according to the present invention, the polymer coated ferrite fine particles being possible to control the particle size uniformly while having high aqueous dispersibility and preferred biomolecule immobilization ability and the easy method for preparing the same may be provided. The polymer coated ferrite fine particles may be expected to be applied in wide area of medical fields.

DESCRIPTION OF SIGNS

50—magnetite fine particle, 52—dextran molecule

The invention claimed is:

1. A method for preparing polymer coated ferrite fine particles, the method comprising:
preparing a mixed aqueous solution by dissolving ferrous iron ion and polyacrylic acid in water;
adding alkaline to the mixed aqueous solution;
adding an oxidizer to the mixed aqueous solution after addition of the alkaline; and
heating the mixed aqueous solution after addition of the oxidizer under pressure at a temperature above 100° C., wherein:
(a) the mixed aqueous solution is prepared in an equivalent ratio of a carboxyl group of the polyacrylic acid to the ferrous iron ion of from 1.2 to 1.8, or
(b) adding the alkaline comprises adjusting the pH of the reaction system to be from 10.5 to 11.0, or
(c) preparing the mixed aqueous solution comprises dissolving at least one kind of metal ion selected from the group consisting of zinc, nickel, cobalt, manganese, barium, rare and earth metal in addition to the ferrous iron ion.

2. The method of claim 1, wherein the temperature lies between 150° C. and 200° C.

3. The method of claim 1, wherein the oxidizer is sodium nitrate.

4. The method of claim 1, wherein the mixed aqueous solution is prepared in an equivalent ratio of a carboxyl group of the polyacrylic acid to the ferrous iron ion of from 1.2 to 1.8.

5. The method of claim 1, wherein the polyacrylic acid has a molecular weight which ranges from 1000 to 4000.

6. The method of claim 1, wherein adding the alkaline comprises adjusting the pH of the reaction system to be from 10.5 to 11.0.

7. The method of claim 1, wherein preparing the mixed aqueous solution comprises dissolving at least one kind of metal ion selected from the group consisting of zinc, nickel, cobalt, manganese, barium, and rare earth metal in addition to the ferrous iron ion.

8. A method for preparing polymer coated ferrite fine particles, the method comprising:
preparing a mixed aqueous solution by dissolving ferrous iron ion and polyacrylic acid in water and then chelating the polyacrylic acid to the ferrous iron ion;
adding alkaline to the mixed aqueous solution;
adding sodium nitrate to the mixed aqueous solution after addition of the alkaline; and
heating the mixed aqueous solution after addition of an oxidizer under pressure at a temperature above 100° C., wherein:
(a) the mixed aqueous solution is prepared in an equivalent ratio of a carboxyl group of the polyacrylic acid to the ferrous iron ion of from 1.2 to 1.8, or
(b) adding the alkaline comprises adjusting the pH of the reaction system to be from 10.5 to 11.0, or
(c) preparing the mixed aqueous solution comprises dissolving at least one kind of metal ion selected from the group consisting of zinc, nickel, cobalt, manganese, barium, rare and earth metal in addition to the ferrous iron ion.

9. Polymer coated ferrite fine particles, the ferrite fine particles being coated with polyacrylic acid and having an average particle size not more than 10 nm, the polymer coated ferrite fine particles having a T1 relaxation performance from 60 to 70 $(mMsec)^{-1}$ and a T2 relaxation performance from 110 and 130 $(mMsec)^{-1}$.

10. An aqueous dispersion comprising the polymer coated ferrite particles of claim 9.

11. An MRI imaging agent comprising the polymer coated ferrite fine particles of claim 9.

12. The polymer coated ferrite fine particles of claim 9, wherein the polymer coated ferrite fine particles are a heat source for hyperthermia therapy.

13. The polymer coated ferrite fine particles of claim 9, wherein the polymer coated ferrite fine particles exhibit a magneto-acoustic effect.

14. Polymer coated ferrite fine particles, the polymer coated ferrite fine particles being prepared by the process of claim 1.

15. The method of claim 4, wherein adding the alkaline comprises adjusting the pH of the reaction system to be from 10.5 to 11.0.

16. The method of claim 4, wherein preparing the mixed aqueous solution further comprises dissolving at least one kind of metal ion selected from the group consisting of zinc, nickel, cobalt, manganese, barium, and rare earth metal in addition to the ferrous iron ion.

17. The method of claim 15, wherein preparing the mixed aqueous solution further comprises dissolving at least one kind of metal ion selected from the group consisting of zinc, nickel, cobalt, manganese, barium, and rare earth metal in addition to the ferrous iron ion.

18. The method of claim 8, wherein the mixed aqueous solution is prepared in an equivalent ratio of a carboxyl group of the polyacrylic acid to the ferrous iron ion of from 1.2 to 1.8.

19. The method of claim 8, wherein adding the alkaline comprises adjusting the pH of the reaction system to be from 10.5 to 11.0.

20. The method of claim 8, wherein preparing the mixed aqueous solution further comprises dissolving at least one kind of metal ion selected from the group consisting of zinc, nickel, cobalt, manganese, barium, and rare earth metal in addition to the ferrous iron ion.

* * * * *